US010508940B2

(12) United States Patent
Faustmann et al.

(10) Patent No.: US 10,508,940 B2
(45) Date of Patent: Dec. 17, 2019

(54) MEASURING DEVICE FOR FLUIDS AS WELL AS FLUIDIC SYSTEM WITH A MEASURING DEVICE

(71) Applicants: Buerkert Werke GmbH & Co. KG, Ingelfingen (DE); Burkert SAS, Triembach-au-Val (FR)

(72) Inventors: Hendrik Faustmann, Ingelfingen (DE); Yannick Fuchs, Triembach-au-Val (FR); Yves Hoog, Triembach-au-Val (FR); Franziska Maier, Ingelfingen (DE); Michael Tischmacher, Ingelfingen (DE)

(73) Assignees: BUERKERT WERKE GMBH & CO. KG (DE); BURKERT S.A.S. (FR)

( * ) Notice: Subject to any disclaimer, the term of this patent is extended or adjusted under 35 U.S.C. 154(b) by 13 days.

(21) Appl. No.: 16/030,915

(22) Filed: Jul. 10, 2018

(65) Prior Publication Data

US 2019/0011299 A1    Jan. 10, 2019

(30) Foreign Application Priority Data

Jul. 10, 2017    (DE) .......................... 10 2017 115 431

(51) Int. Cl.
*G01F 1/66*    (2006.01)

(52) U.S. Cl.
CPC .................... *G01F 1/662* (2013.01)

(58) Field of Classification Search
CPC ....................................... G01F 1/662
See application file for complete search history.

(56) References Cited

U.S. PATENT DOCUMENTS

| 5,090,252 A | 2/1992 | Tschirner |
| 6,026,693 A | 2/2000 | Baumoel et al. |
| 7,647,840 B2 * | 1/2010 | Rickli ..................... G01F 1/662 |
| | | 73/861.12 |

(Continued)

FOREIGN PATENT DOCUMENTS

| DE | 19823165 A1 | 12/1998 |
| EP | 0303255 A1 | 2/1989 |

(Continued)

*Primary Examiner* — Jewel V Dowtin
(74) *Attorney, Agent, or Firm* — Dilworth IP, LLC

(57) ABSTRACT

A measuring device with a fluid module is proposed, which comprises a measuring tube through which a fluid can flow and at least one acoustic measuring unit. The at least one acoustic measuring unit comprises at least one transmitter, at least one receiver as well as at least one waveguide. The measuring tube has at least one measuring section with a substantially angular internal cross section and at least one connecting section with a non-angular internal cross section, wherein the measuring tube has at least one transition section, which extends between the measuring section and the connecting section. The transition section has an internal cross section identical to the internal cross section of the measuring section at an end allocated to the measuring section and further an internal cross section identical to the internal cross section of the connecting section at an end allocated to the connecting section. Furthermore, a fluidic system is described.

19 Claims, 6 Drawing Sheets

(56) References Cited

U.S. PATENT DOCUMENTS

| | | | |
|---|---|---|---|
| 8,844,359 B2* | 9/2014 | Dam | G01N 29/024 |
| | | | 73/597 |
| 9,689,727 B2* | 6/2017 | Kissling | G01F 1/662 |
| 10,190,896 B2* | 1/2019 | Makino | G01K 1/143 |
| 2015/0204704 A1* | 7/2015 | Wiest | G01F 1/662 |
| | | | 73/861.28 |

FOREIGN PATENT DOCUMENTS

| | | |
|---|---|---|
| EP | 0715155 A1 | 6/1996 |
| EP | 1742024 A1 | 1/2007 |

* cited by examiner

MEASURING DEVICE FOR FLUIDS AS WELL AS FLUIDIC SYSTEM WITH A MEASURING DEVICE

FIELD OF THE INVENTION

The invention relates to a measuring device with a fluid module, which comprises a measuring tube through which a fluid can flow and at least one acoustic measuring unit, as well as a fluidic system.

BACKGROUND

Measuring devices for fluids in fluidic systems are used, among other things, in the food and pharmaceutical industries for measuring mass or volumetric flow rates of fluids, in particular of liquids, with high precision. One variant of such measuring devices are so-called SAW flowmeters (surface acoustic wave), which can determine mass and volumetric flow rates of fluids by generating and measuring surface waves. Depending on the design of the SAW flowmeters, other or further properties of the fluid can be measured, for example density, compressibility, sound velocity and acoustic impedance.

In particular in food and pharmaceutical technologies, it is necessary in some fields to meter fluids precisely. For this purpose, it can be necessary to measure a mass or volumetric flow rate precisely.

The object of the invention is therefore to provide a measuring device for fluids, which can determine a mass and/or volumetric flow rate of a fluid with high precision.

SUMMARY

The present invention provides a measuring device of the type mentioned at the beginning, wherein the at least one measuring unit comprises at least one transmitter, at least one receiver as well as at least one waveguide, wherein the measuring tube has at least one measuring section with a substantially angular internal cross section and at least one connecting section with a non-angular internal cross section, wherein the measuring tube has at least one transition section, which extends between the measuring section and the connecting section, and wherein the transition section has an internal cross section identical to the internal cross section of the measuring section at an end allocated to the measuring section and further has an internal cross section identical to the internal cross section of the connecting section at an end allocated to the connecting section. "Substantially angular" means here that there are flat sides, the extension of which to their intersection would result in a simple polygon. In particular, this does not therefore rule out corners of the simple polygon being rounded. With the measuring device according to the invention it is possible for several reasons to determine the mass and/or volumetric flow rate of the fluid precisely. On the one hand, the substantially angular internal cross section by way of the flat sides enables an optimal connection of the acoustic measuring unit to the fluid flowing through, with the result that a defined part of the flow profile is determined. On the other hand, the transition between the non-angular connecting section and the substantially angular measuring section does not take place abruptly over the transition section, which results in low flow separations of the fluid and thus in a low pressure loss and low turbulence.

The measuring section preferably has a substantially rectangular internal cross section, in particular a substantially square one. Substantially rectangular/square means here that there are flat sides, the extension of which to their intersection would result in a rectangle/square. In particular, this does not therefore rule out corners of the rectangle/square being rounded. The acoustic measuring unit is connected to the fluid flowing through particularly well via the flat sides of the measuring section present in the case of a substantially rectangular/square internal cross section.

According to an aspect of the invention it is provided that the internal cross section of the transition section changes continuously over the whole length between the end that is allocated to the measuring section and the end that is allocated to the connecting section. In other words, the transition between areas with different internal cross sections is effected smoothly and without hard, abrupt transitions or transitions with steps. This prevents increased flow separations and thus irregular flow profiles, high turbulence and pressure losses from arising, which can distort measurements.

A further aspect provides that the transition section has an aperture angle between 2° and 10° at least in sections. The small aperture angle ensures a smooth transition, which is thus low in flow separation, between the connecting section and the measuring section.

According to another aspect, the transition section is formed nozzle-shaped. A nozzle-shaped design is particularly suitable for ensuring a transition between connecting section and measuring section which is low in flow separation.

The at least one connecting section preferably has a substantially round, preferably circular internal cross section. Substantially round means here that there are no flat sides. However, the internal cross section of the connecting section can deviate from a circular internal cross section. The measuring tube can be simply connected to external (mostly round) tubes via the round connecting section.

According to an embodiment of the invention, the measuring tube is formed in one piece with the measuring section, the transition section and/or the connecting section. Thereby, firstly the assembly effort is reduced and secondly the measuring tube is particularly leakproof.

It is preferably provided that the measuring tube has a second connecting section and a second transition section, which extends between the measuring section and the connecting section, wherein the second transition section has an internal cross section identical to the internal cross section of the measuring section at an end allocated to the measuring section and further has an internal cross section identical to the internal cross section of the second connecting section at an end allocated to the second connecting section, in particular wherein the internal cross section of the second transition section changes continuously over the whole length between the end that is allocated to the measuring section and the end that is allocated to the second connecting section. A drop in pressure, turbulence and thus possibly distortion of the measurements caused by flow separations are also thereby reliably prevented at the end of the measuring tube which lies opposite the first connecting section.

Further preferably, the second connecting section and/or the second transition section is/are formed mirror-symmetrical with respect to the first connecting section and to the first transition section, respectively. The measuring device thereby has no preferred direction with respect to a direction of flow. For this reason, the measuring device can be used for measurements irrespective of its direction of installation.

According to an aspect of the invention, it is provided that the waveguide is provided on the measuring tube, in particular is formed integrally with the measuring tube. If the measuring tube is formed integrally with the waveguide, the measuring device is structurally simpler and, in addition, disruptive reflections of waves at a boundary surface between waveguide and wall of the measuring tube are avoided.

According to a further aspect of the invention, the waveguide is provided on the measuring section. In particular, the waveguide is formed integrally with a side wall of the measuring section. The measuring device is also thereby structurally simpler and, in addition, disruptive reflections of waves at a boundary surface between waveguide and side wall of the measuring section are also avoided here.

The waveguide preferably extends from the at least one transmitter to the at least one receiver. Surface waves can thereby propagate without interruption from the transmitter to the receiver.

An embodiment of the invention provides that the at least one waveguide has a substantially constant thickness, in particular is formed flat. This embodiment is particularly advantageous for a propagation of surface waves. Disruptive reflections of surface waves occur at points with steps/changes in the wall thickness, which is avoided by a constant wall thickness.

In each case at least one transmitter and at least one receiver is preferably provided on at least two side surfaces adjoining each other in the circumferential direction of the measuring tube or on two side surfaces of the measuring tube lying opposite each other. Measurements can thereby also be carried out when the measuring tube is not completely filled with a fluid. In particular, a fill level of the fluid in the measuring tube can thereby be determined. The measurement of the flow rate in partially filled tubes is thus also possible.

The at least one transmitter and the at least one receiver can be formed structurally identical. The transmitter can thereby also act as receiver and the receiver can also act as transmitter. The reversibility of the transmission direction is of importance in the measurement of different quantities, for example in determining a mass and/or volumetric flow rate.

An embodiment of the invention provides that the at least one connecting section has a larger internal cross-sectional area than the at least one measuring section. It is thereby ensured that a fill level of the measuring section corresponds at least to that of the connecting section. In particular, the measuring section is completely filled when this is also true of the connecting section.

A ratio of the internal cross-sectional areas of the at least one connecting section and the measuring section can be between 1.3 and 0.5 $\pi$, preferably between 1.4 and 1.56. The connecting section and the measuring section are in particular arranged concentrically with respect to each other. In other words, central axes which define the connecting section and the measuring section coincide.

According to an aspect, a fluid connection is provided on the at least one connecting section, in particular wherein the fluid connection is formed in one piece with the at least one connecting section. The measuring device can be connected to an external fluid source via the fluid connection.

In a preferred embodiment of the invention, the measuring tube has at least one circumferential section on the inner surface which, seen in the longitudinal direction of the measuring tube, runs linearly along the whole length of the measuring tube. The measuring tube is installed in the measuring device such that this circumferential section is arranged at the bottom in relation to a direction predetermined by gravity, thus at minimal gravitational potential, when the measuring device is used. The measuring tube is thus self-emptying as liquid cannot collect anywhere. This linear circumferential section preferably also extends beyond the fluid connections, with the result that it runs continuously from one end of the measuring tube to the opposite end, including fluid connections.

Further preferably, the circumferential section of the inner surface of the measuring tube runs along an angle of the inner surface of the measuring section. No areas can thereby form in the measuring device from which the fluid cannot run out, even when the angle does not point exactly downwards (in the sense mentioned above). A certain tolerance with respect to the installation position of the measuring tube is thus possible.

According to an embodiment of the invention, angles of the inner surface of the measuring section are rounded. This is of great importance in particular when the measuring device is used in areas which must comply with strict hygiene regulations. The measuring tube can be emptied and/or cleaned more easily as a result of the rounded angles. Furthermore, the deposition of impurities is thereby hindered. In other words, the angles are provided with a radius which can be, for example, between 0.5 and 15 mm, preferably between 0.8 and 5 mm.

An aspect provides that, in the longitudinal direction of the measuring tube, in each case a damping element is provided between the transmitter and an end of the measuring tube close to the transmitter as well as between the receiver and an end of the measuring tube close to the receiver. The damping elements damp disruptive reflections of surface waves at ends of the measuring tube or in areas with changes in the wall thickness, for example at the ends of the measuring section.

Preferably, the damping elements have in each case at least one side which is arranged angled with respect to the longitudinal direction of the measuring tube, in particular wherein the damping elements are formed triangular or arrow-shaped. Interfering waves are thus deflected to the side and not simply reflected, which further reduces undesired interfering signals.

In an embodiment of the invention, in each case a further damping element is provided on the transmitter and on the receiver. Disruptive reflections of surface waves are further reduced by the additional damping elements.

The transmitter and/or the receiver can extend over 50 to 100 percent of a height of the measuring section, preferably over 80 to 100 percent. An available surface area is thereby optimally utilized.

In particular in the longitudinal direction of the measuring tube, the transmitter and the receiver are spaced apart from each other by at least a width of the measuring section.

It can further be provided that the measuring device has an electronics module. The electronics module can comprise electrical interfaces, further electronic components, an electronics housing and a user interface.

The invention further relates to a fluidic system with a measuring device for measuring the fluid, wherein the fluidic system has a fluid channel with a measuring section and the fluid channel is angular in cross section. The corners are formed by angles of the fluid channel wall, wherein one of the angles forms the lowest point of the channel in the vertical direction. In other words, the angle is the lowest point of the fluid channel in the area of the measuring device, whereby the outward flow of fluid to empty the fluid channel is significantly better than in the case of, for example, round cross sections or angular cross sections, in which the angle is not towards the bottom.

DETAILED DESCRIPTION

Figure 1:
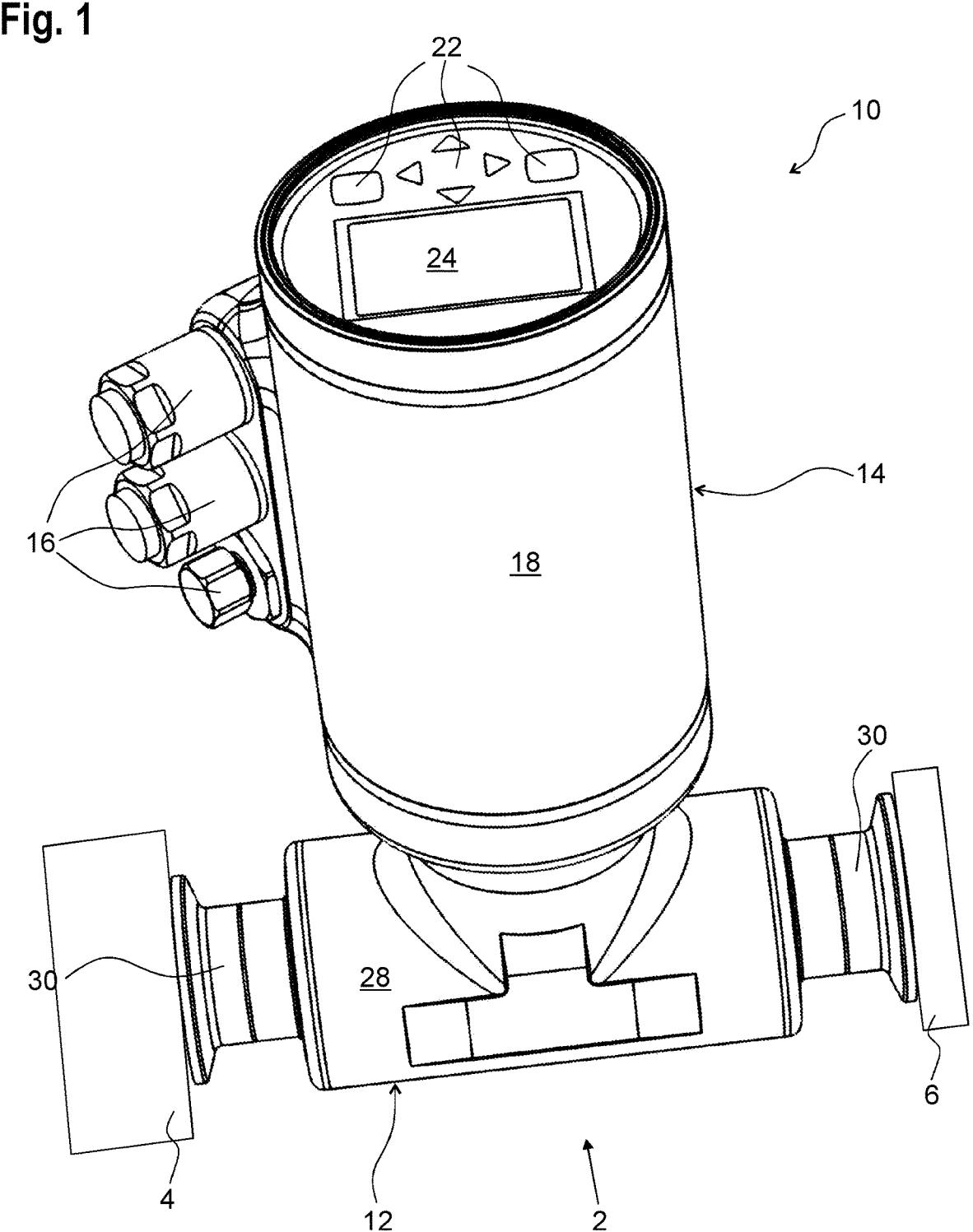
FIG. 1 shows a measuring device according to the invention as part of a fluidic system according to the invention in a perspective view.

In FIG. 1 a fluidic system 2 is represented, for example in the pharmaceutical industry, which is represented symbolically by two system halves 4, 6. A measuring device 10 is arranged between the system halves 4, 6, which fluidically connects the system halves 4, 6. Of course, the system halves 4, 6 can and may also still be connected by other channels or lines.

The measuring device 10 is provided for fluids, in particular for liquids.

The measuring device 10 can have a fluid flowing through it and is used to measure a mass and/or volumetric flow rate as well as further properties of the fluid. The measuring device 10 uses surface acoustic waves (SAW), more precisely Lamb waves, to measure the above-named quantities.

The measuring device 10 comprises a fluid module 12 and an electronics module 14, wherein the two modules 12, 14 are preferably rigidly connected to each other.

Figure 2:
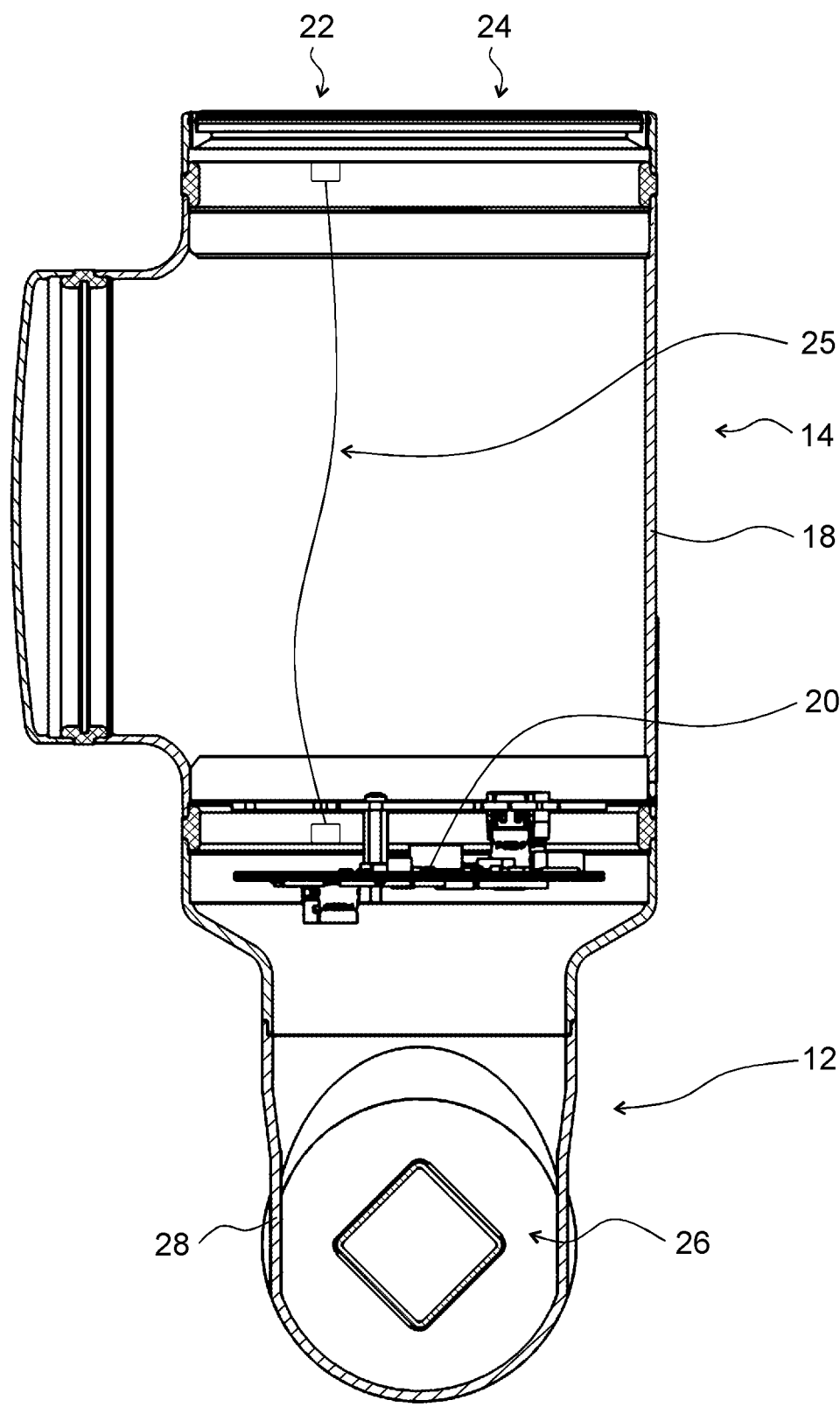
FIG. 2 shows a cross section through the measuring device from FIG. 1.

The electronics module 14 has electrical interfaces 16 and an electronics housing 18, in which various electronic components 20 can be housed (see FIG. 2). Control elements 22 and/or at least one display element 24 are further provided on the electronics housing 18. The control elements 22 and/or the at least one display element 24 are connected to the electronic components 20 in a signal-transmitting manner via an electronic connecting element 25.

Figure 3:
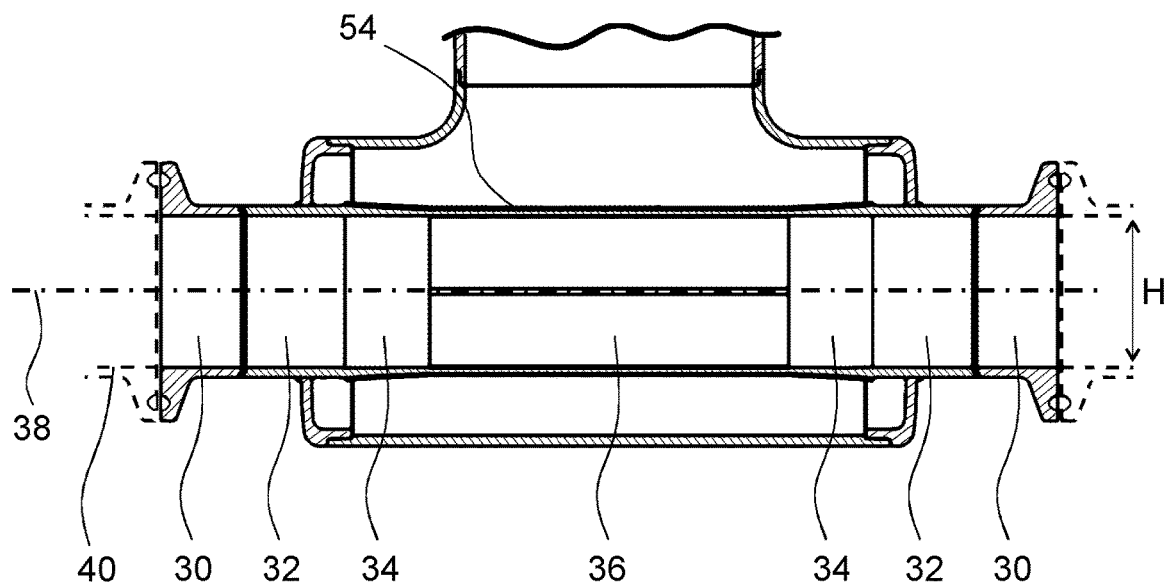
FIG. 3 shows a longitudinal section through a fluid module of the measuring device from FIG. 1.

The fluid module 12 comprises a measuring tube 26 with a fluid channel inside it, a housing 28 as well as fluid connections 30 (see FIG. 3). The fluid connections 30 are attached to the measuring tube 26 in a fluid-tight manner. The measuring tube 26 can also be formed in one piece with the fluid connections 30.

In FIG. 3, the measuring tube of the fluid module 12 is shown in a longitudinal section. The measuring tube 26 comprises essentially three different types of areas: two connecting sections 32 are provided, wherein each of the connecting sections 32 is allocated in each case to one fluid connection 30 and serves to connect the measuring tube 26 to it. The measuring tube 26 can therefore be connected to a fluid flow via the fluid connections 30. On the other side, two transition sections 34 and a measuring section 36 are provided, wherein in each case one transition section 34 is allocated to a connecting section 32 and runs between the allocated connecting section 32 and the measuring section 36. In each case one end of the measuring section 36 is allocated to a transition section 34.

In particular, the measuring tube 26 is formed in one piece with the measuring section 36, the transition sections 34 and/or the connecting sections 32.

In the embodiment shown here, the measuring tube 26 is formed mirror-symmetrical with respect to a plane which intersects the measuring tube 26 axially in the centre and stands perpendicularly on a central axis 38 defined by the measuring tube 26. The measuring tube 26 can thereby be used irrespective of a direction of flow of the fluid.

The connecting sections 32 have an internal cross section that is identical to the fluid connections 30. This internal cross section is round, in particular circular. In contrast, the internal cross section of the measuring section 36 is substantially angular, in particular substantially rectangular. In the embodiment shown here, the internal cross section of the measuring section is substantially square. Substantially angular/rectangular/square means here that there are flat sides, the extension of which to their intersection would result in a simple polygon/rectangle/square. In particular, this does not therefore rule out corners of the simple polygon being rounded.

The internal cross section of the transition sections 34 changes over the length of the transition sections 34 in such a way that the transition sections 34 have an internal cross section which is identical to the internal cross section of the connecting sections 32 in each case at an end allocated to the connecting sections 32, and that the transition sections 34 have an internal cross section which is identical to the internal cross section of the measuring section 36 in each case at an end allocated to the measuring section 36. This means there is no shoulder or cross-sectional step present.

The change in the internal cross section of the transition sections 34 takes place continuously over the whole length of the transition sections 34. In particular, the transition sections 34 are designed in such a way that flow separations of the fluid flowing through do not occur, whereby a drop in pressure and additional turbulence is avoided. This can be achieved, for example, by a small aperture angle α of the transition sections 34 from 2° to 10° or by a nozzle-shaped design of the transition sections 34.

Figure 9:
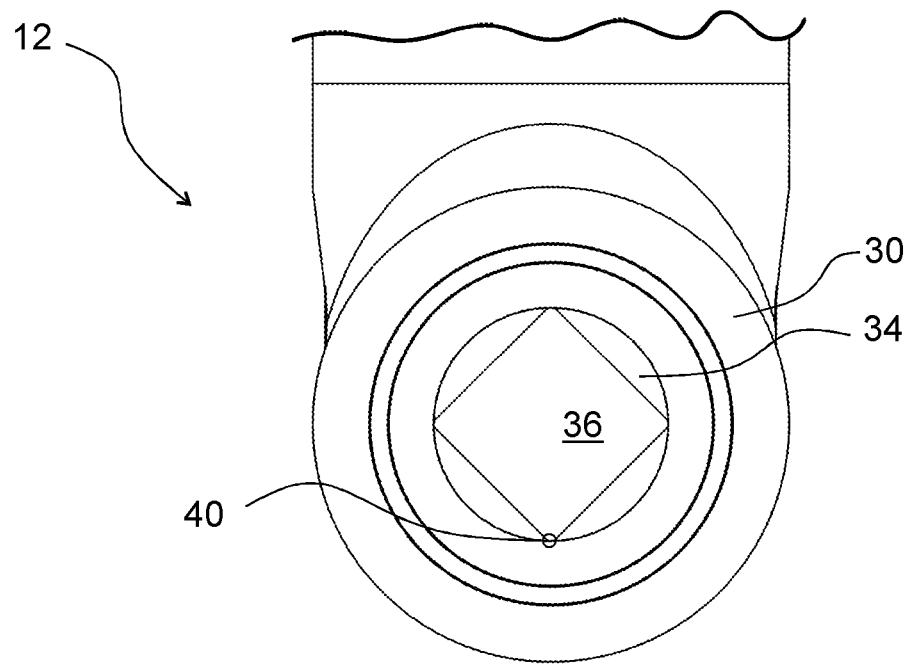
FIG. 9 shows a schematic view of the measuring tube from FIG. 1 in the axial direction of the measuring tube.

The measuring section 36 has a smaller internal cross-sectional area than the connecting sections 32. It is thereby always ensured that the measuring section 36 is completely filled with the fluid when this is also the case for the connecting sections 32. A ratio of the internal cross-sectional areas of the connecting sections 32 and the measuring section 36 is in each case, for example, between 1.3 and 0.5 π, preferably between 1.4 and 1.56. As shown in FIG. 9, the measuring section 36 and the connecting sections 32 are arranged concentrically, i.e. the central axes which they define in each case coincide.

Figure 10:
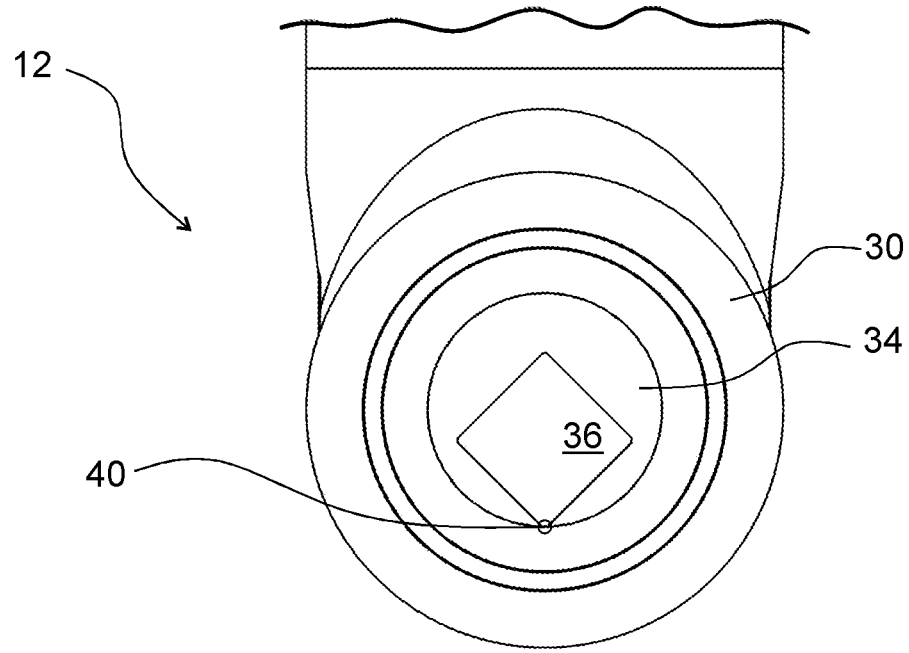
FIG. 10 shows a schematic view of the measuring tube from FIG. 1 in the axial direction of the measuring tube according to an alternative embodiment.

Alternatively, the ratio of the internal cross-sectional areas of the connecting sections 32 and the measuring section 36 can be more than 0.5 π. In this case, the connecting sections 32 and the measuring section 36 are in each case arranged eccentrically with respect to each other, as shown in FIG. 10. Then, the central axes which they define in each case do not therefore coincide. An eccentric arrangement is necessary in this case in order to make the circumferential section of the measuring tube 26, which runs along the straight line 40, possible at all.

The measuring tube 26 has at least one circumferential section on the inner surface, which, seen in the longitudinal direction of the measuring tube 26 (therefore along the central axis 38), runs linearly along the whole length of the measuring tube 26. In other words, there is at least one straight line 40, along which a circumferential section of the measuring tube 26 runs between the two ends of the measuring tube 26 over the whole length of the measuring tube 26. The measuring tube 26 is installed in the measuring device 10 such that this circumferential section is arranged at the bottom in relation to a direction predetermined by gravity, thus at minimal gravitational potential, when the measuring device 10 is used. The measuring tube is thus self-emptying as liquid cannot collect anywhere.

The at least one straight line 40 preferably runs along an angle 42 of the internal cross section of the measuring section 36. As can be seen particularly well in FIGS. 9 and 10, the angle 42 is then arranged at the low point of the fluid channel in the measuring section 36. It can also be provided that such a straight line exists along several of the angles 42. Therefore, the measuring tube 26 then has several circumferential sections, which run linearly along the whole length of the measuring tube 26. The measuring tube 26 thereby has several installation positions in which it is self-emptying.

The angles 42 of the internal cross section of the measuring section 36 are rounded, thus provided with a radius. For example, the radius can be between 0.5 mm and 15 mm, preferably between 0.8 mm and 5 mm. Because of the rounded angles 42, liquids cannot collect in the measuring section 36. The measuring tube 26 is accordingly even easier to empty. This is advantageous above all in hygienic applications, for example in food and/or pharmaceutical technology. In addition, there is thereby a certain tolerance of the measuring tube 26 with respect to the direction of installation within which the measuring tube 26 is self-emptying.

Figure 4:
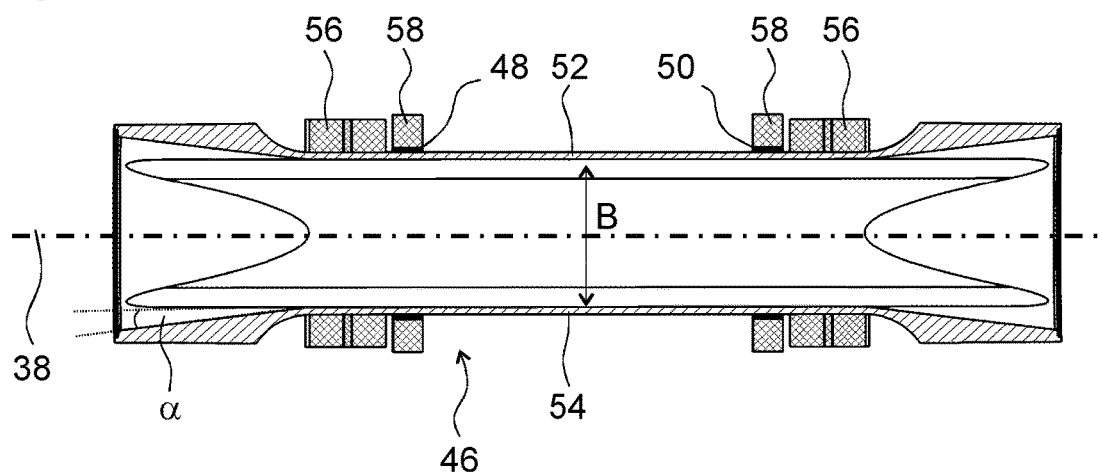
FIG. 4 shows a longitudinal section through the measuring tube, rotated by 45° compared with the longitudinal section shown in FIG. 3.
Figure 5:
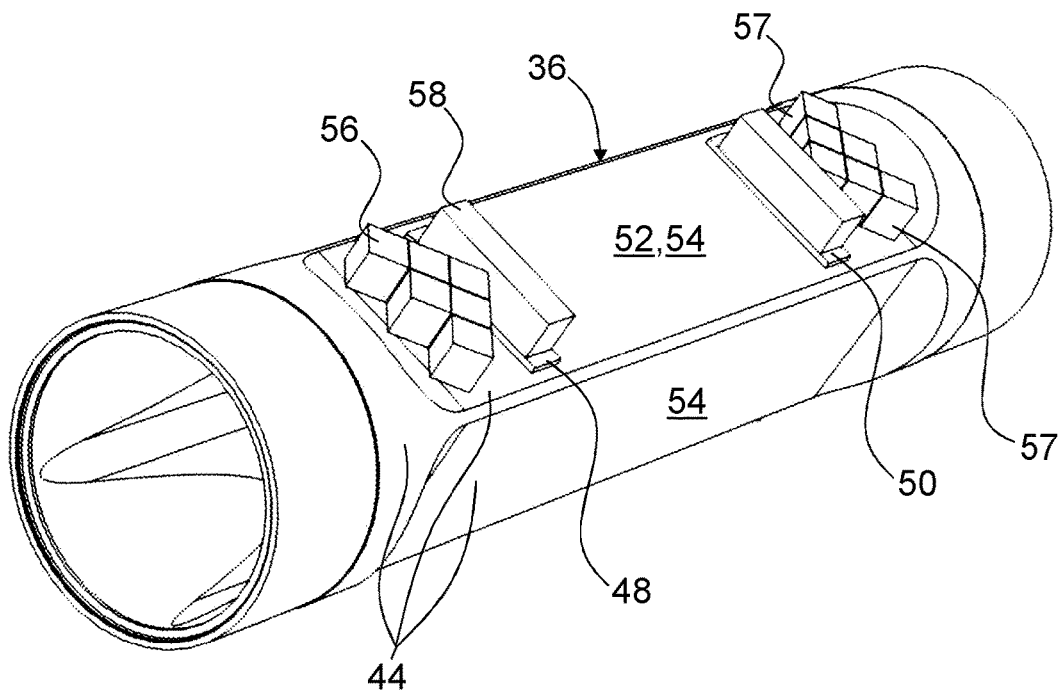
FIG. 5 shows a measuring tube of the measuring device from FIG. 1 in a perspective view.
Figure 6:
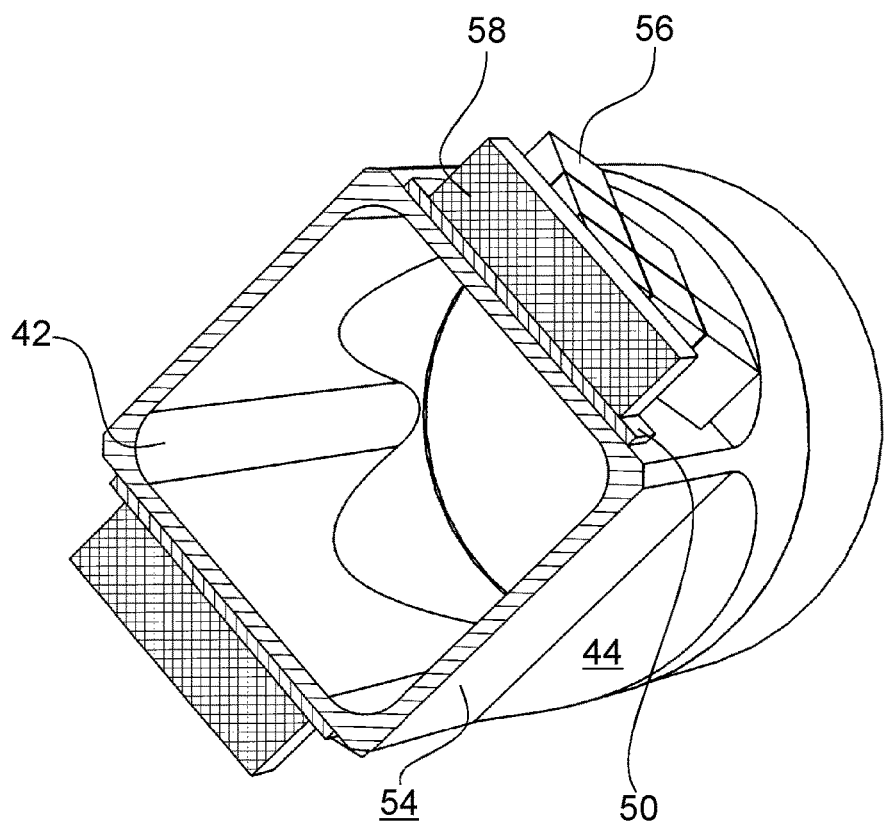
FIG. 6 shows a cross section through the measuring tube from FIG. 5 in a perspective view.

As can be seen particularly well in FIGS. 4 to 6, at least one acoustic measuring device 46 is attached to an outer surface 44 of the measuring tube 26 in the area of the measuring section 36. The acoustic measuring device 46 comprises a transmitter 48, a receiver 50 and a waveguide 52, which extends at least from the transmitter 48 to the receiver 50. The waveguide 52 is formed integrally with one of the side walls 54 of the measuring section 36. In other words, the side wall 54 here forms the waveguide 52.

The waveguide 52 has a substantially constant thickness and in particular is formed flat. This embodiment is particularly advantageous for a propagation of surface waves. At points with steps/changes in the wall thickness, disruptive reflections and dispersions of surface waves occur, which is prevented by a constant wall thickness.

The transmitter 48 and the receiver 50 extend in each case over 50 to 100 percent of the height H of the measuring section, preferably over 80 to 100 percent.

The transmitter 48 and the receiver 50 are further spaced apart from each other by at least a width B of the measuring section 36.

The transmitter 48 is formed to induce surface waves in the waveguide 52. These are, in particular, Lamb waves. The surface waves propagate in the waveguide 52 starting from the transmitter 48 to the receiver 50. The surface waves also couple out into the fluid flowing through the measuring tube at an angle which is dependent on the fluid and on the flow rate of the fluid. The coupled-out waves travel through the fluid at least once but can also travel through it several times. Some of the coupled-out waves couple into the waveguide 52 again and travel further to the receiver. Conclusions on properties of the fluid, for example on the fluid density, can be drawn from a difference in transit time between surface waves, which have propagated directly from the transmitter 48 to the receiver 50, and waves, which have passed through the fluid.

The transmitter 48 and the receiver 50 are formed structurally identical, with the result that the transmitter 48 can also function as receiver and the receiver 50 can also function as transmitter. The above-described procedure can thereby also be repeated in the reverse direction. Conclusions can then be drawn on a mass and/or volumetric flow rate of the fluid from a difference in transit times between the two transmission directions.

Signals received by the receiver 50 are passed on to the electronic components 20 and processed by them. The electronic components 20 are also, in particular, formed to control transmitter 48 and receiver 50.

On the basis of the above-named measured quantities, deposits and/or abrasions in the measuring tube 26 can also be identified and taken into consideration. In addition, it is possible to detect gas bubbles.

A damping element 56 is arranged in each case between the transmitter 48 and an end of the measuring section 36 close to the transmitter as well as between the receiver 50 and an end of the measuring section 36 close to the receiver. The damping elements 56 here are constructed in each case in several pieces and have two side surfaces 57 arranged angled with respect to the central axis 38. In general, damping elements can also be formed in one piece. More precisely, the damping elements 56 here are constructed in each case in the shape of an arrow. Alternatively, the damping elements 56 can also be constructed in the shape of a triangle or other geometric figures. Further, in each case a further damping element 58 is provided on the transmitter 48 and on the receiver 50. The damping elements 56, 58 damp disruptive reflections, which occur, for example, at the ends of the measuring tube 26 and in particular also at the end of the measuring section 36 because of a changing wall thickness. In addition, the side surfaces 57 of the damping elements 56 arranged angled with respect to the central axis 38 also deflect arriving surface waves laterally, whereby they are not completely reflected back to the receiver 50. This additionally reduces interfering signals occurring in an undesired manner.

Figure 7:
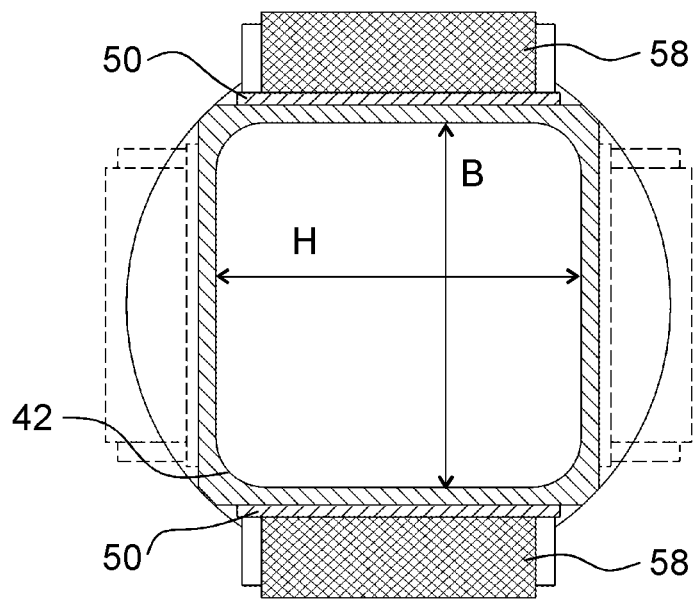
FIG. 7 shows a cross section through the measuring tube from FIG. 5.

As indicated in FIG. 7, it can also be provided that several pairs of transmitters 48 and receivers 50 are provided on side walls 54 adjoining each other in relation to the circumferential direction of the measuring tube 26, or on side walls 54 lying opposite each other. The measuring device 10 can thereby also be used for measurements when the measuring tube 26, in particular the measuring section 36, is not completely filled with fluid. In particular, a fill level of the fluid in the measuring section 36 can thereby be determined.

Figure 8:
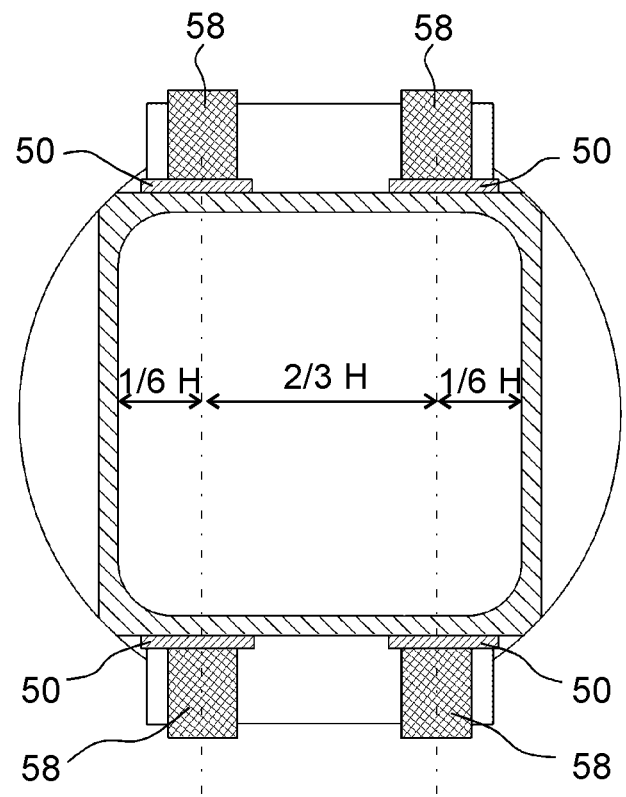
FIG. 8 shows a cross section through the measuring tube from FIG. 5 in an alternative embodiment.

Moreover, the transmitters 48 and the receivers 50 can in each case be constructed in several pieces, as shown in FIG. 8. In this case, the individual pieces of the transmitters 48 or of the receivers 50, respectively, are in each case spaced apart from each other by approximately ⅔ of the width of the internal cross section of the measuring section 36.

It can be provided that the measuring device has several operating modes. The several operating modes can differ from each other, for example, in quantities to be measured. In particular, it can be provided that a user can switch between the several operating modes using the control elements 22. It can further be provided that one or more measured quantities are displayed on the display element 24.

For example, the user can also select via the control elements 22 which measured quantity or quantities is or are displayed.

The invention claimed is:

1. Measuring device with a fluid module, which comprises a measuring tube through which a fluid can flow and at least one acoustic measuring unit,
    wherein the at least one acoustic measuring unit comprises at least one transmitter, at least one receiver as well as at least one waveguide,
    wherein the measuring tube has at least one measuring section with a substantially angular internal cross section and at least one connecting section with a non-angular internal cross section,
    wherein the measuring tube has at least one transition section, which extends between the measuring section and the connecting section, and
    wherein the transition section has an internal cross section identical to the internal cross section of the measuring section at an end allocated to the measuring section and further has an internal cross section identical to the internal cross section of the connecting section at an end allocated to the connecting section.

2. Measuring device according to claim 1, wherein the measuring section has a substantially rectangular internal cross section and/or the at least one connecting section has a substantially round internal cross section.

3. Measuring device according to claim 1, wherein the internal cross section of the transition section changes continuously over the whole length between the end that is allocated to the measuring section and the end that is allocated to the connecting section.

4. Measuring device according to claim 1, wherein the measuring tube has a second connecting section and a second transition section, which extends between the measuring section and the second connecting section,
    wherein the second transition section has an internal cross section identical to the internal cross section of the measuring section at an end allocated to the measuring section and further has an internal cross section identical to the internal cross section of the second connecting section at an end allocated to the second connecting section.

5. Measuring device according to claim 4, wherein the second connecting section and/or the second transition section is/are formed mirror-symmetrical with respect to the first connecting section and to the first transition section, respectively.

6. Measuring device according to claim 1, wherein the waveguide is provided on the measuring tube.

7. Measuring device according to claim 1, wherein the waveguide is provided on the measuring section.

8. Measuring device according to claim 1, wherein the waveguide extends from the at least one transmitter to the at least one receiver.

9. Measuring device according to claim 1, wherein the at least one waveguide has a substantially constant thickness.

10. Measuring device according to claim 1, wherein in each case at least one transmitter and at least one receiver are provided at least on two side surfaces adjoining each other in the circumferential direction of the measuring tube or on two side surfaces of the measuring tube lying opposite each other.

11. Measuring device according to claim 1, wherein the at least one connecting section has a larger internal cross-sectional area than the at least one measuring section.

12. Measuring device according to claim 11, wherein a ratio of the internal cross-sectional areas of the at least one connecting section and the at least one measuring section is between 1.3 and 0.5 $\pi$.

13. Measuring device according to claim 1, wherein a fluid connection is provided on the at least one connecting section.

14. Measuring device according to claim 1, wherein the measuring tube has at least one circumferential section on the inner surface which, seen in the longitudinal direction of the measuring tube, runs linearly along the whole length of the measuring tube.

15. Measuring device according to claim 14, wherein the circumferential section of the inner surface of the measuring tube runs along an angle of the inner surface of the measuring section.

16. Measuring device according to claim 1, wherein angles of the inner surface of the measuring section are rounded.

17. Measuring device according to claim 1, wherein, in the longitudinal direction of the measuring tube, in each case a damping element is provided between the transmitter and an end of the measuring tube close to the transmitter as well as between the receiver and an end of the measuring tube close to the receiver.

18. Measuring device according to claim 17, wherein the damping elements have in each case at least one side which is arranged angled with respect to the longitudinal direction of the measuring tube.

19. Measuring device according to claim 1, wherein in each case a further damping element is provided on the transmitter and on the receiver.

* * * * *